(«12») United States Patent
Jamison et al.

(10) Patent No.: US 10,591,395 B1
(45) Date of Patent: *Mar. 17, 2020

(54) LUBRICITY TESTING WITH SHEAR STRESS SENSORS

(71) Applicant: Halliburton Energy Services, Inc., Houston, TX (US)

(72) Inventors: Dale E. Jamison, Humble, TX (US); Andrew D. Vos, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/510,002

(22) Filed: Jul. 12, 2019

(51) Int. Cl.
*G01N 11/14* (2006.01)
*G01N 19/02* (2006.01)

(52) U.S. Cl.
CPC ............ *G01N 11/14* (2013.01); *G01N 19/02* (2013.01)

(58) Field of Classification Search
None
See application file for complete search history.

(56) References Cited

U.S. PATENT DOCUMENTS

| | | | |
|---|---|---|---|
| 3,304,528 A | 2/1967 | Rastrelli et al. | |
| 3,827,294 A | 8/1974 | Anderson | |
| 3,876,972 A | 4/1975 | Garrett | |
| 4,062,225 A | 12/1977 | Murphy, Jr. et al. | |
| 4,483,197 A * | 11/1984 | Kellner | G01N 3/10 |
| | | | 73/150 R |
| 4,592,226 A * | 6/1986 | Weber | G01N 33/383 |
| | | | 73/54.03 |
| 4,811,597 A * | 3/1989 | Hebel | E21B 47/0006 |
| | | | 73/152.48 |
| 5,163,317 A * | 11/1992 | Ono | G01N 11/142 |
| | | | 73/54.32 |
| 5,199,298 A | 4/1993 | Ng et al. | |

(Continued)

FOREIGN PATENT DOCUMENTS

| | | |
|---|---|---|
| EP | 1712890 A2 | 10/2006 |
| WO | 2008022960 A1 | 2/2008 |
| WO | 2014150051 A1 | 9/2014 |

OTHER PUBLICATIONS

Acknowledgement receipt and specification for patent application entitled "Fluid Analysis Devices with Shear Stress Sensors," by Dale E. Jamison, et al., filed Jul. 12, 2019 as U.S. Appl. No. 16/510,014.

(Continued)

*Primary Examiner* — Paul M. West
*Assistant Examiner* — Mark A Shabman
(74) *Attorney, Agent, or Firm* — Conley Rose, P.C.; Rodney B. Carroll (57) ABSTRACT

In some examples, a lubricity testing device comprises a fluid tank and a rotational assembly positioned within the fluid tank. The rotational assembly, in turn, comprises a first shaft, a second shaft positioned within the first shaft, and a flexible coupling positioned between the first and second shafts. The flexible coupling is coupled to a first surface of the first shaft and to a second surface of the second shaft. The rotational assembly further comprises a shear stress sensor abutting the flexible coupling. The lubricity testing device also includes a test specimen abutting the rotational assembly.

20 Claims, 5 Drawing Sheets

(56) References Cited

U.S. PATENT DOCUMENTS

| | | |
|---|---|---|
| 6,341,532 B1 | 1/2002 | Xu et al. |
| 6,418,776 B1 | 7/2002 | Gitis et al. |
| 6,426,796 B1 | 7/2002 | Pulliam et al. |
| 6,499,336 B1 | 12/2002 | Raffer |
| 6,575,025 B1 | 6/2003 | Demia |
| 6,629,451 B1 | 10/2003 | Taylor |
| 6,817,223 B2 * | 11/2004 | Lenz ................ G01N 19/02 73/10 |
| 7,311,009 B2 | 12/2007 | Kotovsky |
| 7,338,202 B1 | 3/2008 | Kapat et al. |
| 7,526,941 B2 | 5/2009 | Doe |
| 7,701,586 B2 | 4/2010 | Otugen et al. |
| 7,757,552 B2 | 7/2010 | Bogath et al. |
| 8,375,771 B1 * | 2/2013 | Bi ................ G01N 11/14 73/54.33 |
| 8,794,051 B2 | 8/2014 | Morgan et al. |
| 9,175,557 B2 | 11/2015 | Iversen et al. |
| 9,243,882 B2 | 1/2016 | Brookfield |
| 9,376,906 B2 | 6/2016 | Dalvi et al. |
| 9,625,333 B2 | 4/2017 | Jentoft et al. |
| 9,771,790 B2 | 9/2017 | Clark et al. |
| 10,024,776 B2 | 7/2018 | Khosla et al. |
| 10,132,733 B2 | 11/2018 | Vinogradov-Nurenberg et al. |
| 2002/0070050 A1 | 6/2002 | Wassell |
| 2003/0154772 A1 * | 8/2003 | Jackson ............ G01N 11/14 73/54.28 |
| 2004/0173009 A1 * | 9/2004 | Doe ................ G01D 3/022 73/54.02 |
| 2008/0092641 A1 | 4/2008 | Cahill et al. |
| 2009/0188304 A1 * | 7/2009 | Eskin ............ G01N 11/14 73/54.35 |
| 2016/0109348 A1 | 4/2016 | Robert et al. |
| 2017/0122820 A1 * | 5/2017 | Peng ............ G01L 1/144 |
| 2018/0038780 A1 * | 2/2018 | Yang ............ G01L 1/00 |
| 2018/0252600 A1 | 9/2018 | Sheplak et al. |

OTHER PUBLICATIONS

Acknowledgement receipt and specification for patent application entitled "Measurement of Torque with Shear Stress Sensors," by Dale E. Jamison, et al., filed Jul. 12, 2019 as U.S. Appl. No. 16/510,016.

Acknowledgement receipt and specification for patent application entitled "Measurement of Torque with Shear Stress Sensors," by Andrew D. Vos, et al., filed Jul. 12, 2019 as U.S. Appl. No. 16/510,023.

Office Action dated Aug. 30, 2019 (25 pages), U.S. Appl. No. 16/510,023, filed Jul. 12, 2019.

Office Action dated Sep. 11, 2019 (20 pages), U.S. Appl. No. 16/510,016, filed Jul. 12, 2019.

Office Action dated Sep. 18, 2019 (19 pages), U.S. Appl. No. 16/510,014, filed Jul. 12, 2019.

* cited by examiner

LUBRICITY TESTING WITH SHEAR STRESS SENSORS

BACKGROUND

The properties of drilling fluids are often studied during drilling operations to adjust and improve the drilling operations. The lubricity of drilling fluid is one such frequently studied property. The lubricity of a particular fluid may be tested in the laboratory context using a lubricity testing device, in which the potential impact of the fluid on the friction between a drill string and a borehole wall or other solids may be evaluated. By measuring the lubricity of a particular fluid, drilling operations can be enhanced, for example by altering the composition of the fluid.

BRIEF DESCRIPTION OF THE DRAWINGS

For a detailed description of various examples, reference will now be made to the accompanying drawings in which.

DETAILED DESCRIPTION

Disclosed herein are various examples of a lubricity testing device (LTDs) that uses a shear stress sensor (e.g., a micro-electro-mechanical system (MEMS) shear stress sensor) to measure shear stress that is generated in response to friction between two members of the LTD. The shear stress measurement is used to calculate a coefficient of the friction between the two members of the LTD. Because this friction is impacted by the lubricity of the fluid being tested, the coefficient of friction is a direct indication of the lubricity of the fluid being tested.

More specifically, an example lubricity testing device includes a fluid tank and a rotational assembly positioned within the fluid tank. The rotational assembly includes a first shaft, a second shaft positioned within the first shaft, and a flexible coupling positioned between the first and second shafts. The flexible coupling comprises a rubber-like material, such as silicone rubber. The flexible coupling couples to a first surface of the first shaft and to a second surface of the second shaft. A shear stress sensor (e.g., a MEMS shear stress sensor) abuts the flexible coupling. The device also includes a test specimen, such as a filter cake, abutting the rotational assembly. Fluid is added to the fluid tank and the rotational assembly is rotated against the test specimen. As the rotational assembly rotates, solids and other materials accumulate on the surface of the test specimen at the interface between the rotational assembly and the test specimen, while non-solid elements of the fluid pass through the test specimen as filtrate. The friction between the rotational assembly and the test specimen (including the solids and other materials accumulating on the test specimen) imparts shear stress to the flexible coupling, and the shear stress sensor measures this shear stress. The measured shear stress may be used to calculate the coefficient of friction between the rotational assembly and the test specimen, thus determining the lubricity of the fluid in the fluid tank.

Figure 1:
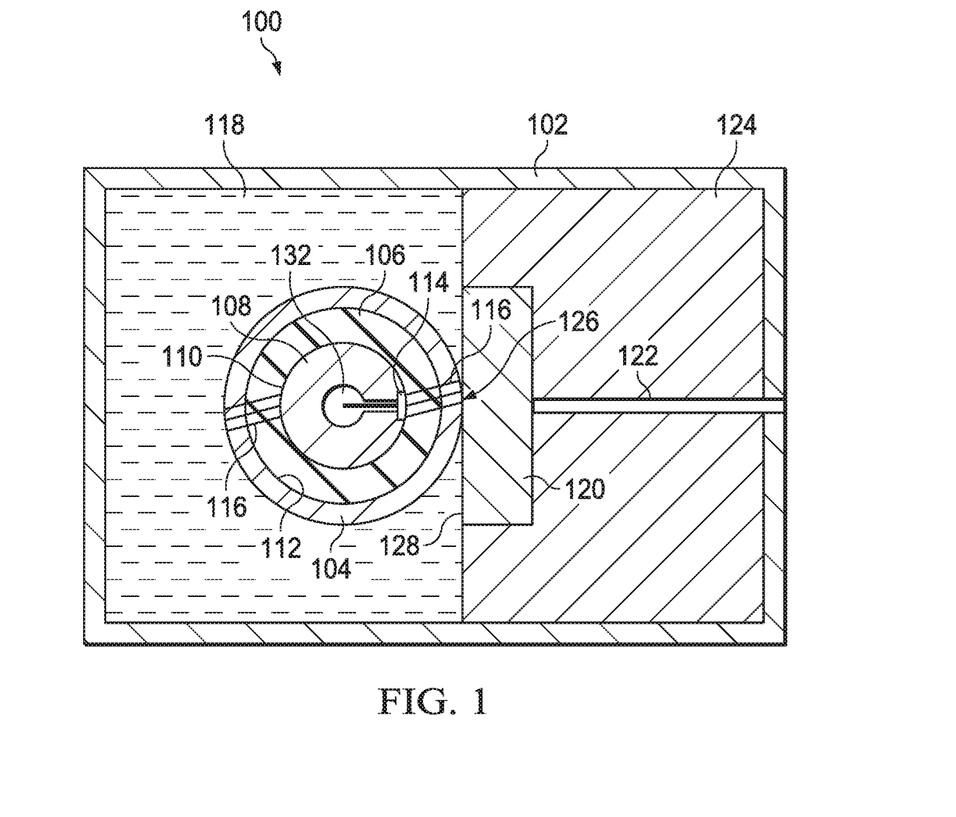
FIG. 1 is a top-down cross-sectional view of a lubricity testing device, in accordance with various examples.

FIG. 1 is a top-down cross-sectional view of a lubricity testing device (LTD) 100, in accordance with various examples. The LTD 100 comprises a housing 102 that includes a fluid tank 118 storing a fluid to be tested. In the fluid tank 118 is a rotational assembly that includes a shaft 108 positioned within a shaft 104. The shaft 108 has an outer surface 110 facing away from a longitudinal axis of the rotational assembly, and the shaft 104 has an inner surface 112 facing toward the longitudinal axis of the rotational assembly. A flexible coupling 106 is positioned between the shafts 104 and 108. The flexible coupling 106 couples to the surfaces 110, 112. Examples of the flexible coupling 106 include: silicone rubber; urethane rubber; natural rubber (polyisoprene); styrene-butadiene-rubber; ethylene propylene diene monomer rubber (EPDM); butylrubber; polyurethane; NEOPRENE CR® (polychloroprene); hydrogenated nitrile; HYPALON® chlorosulphonated polyethylene; nitrile; VITON®; fluorosilicone; and fluorocarbon. Other examples are contemplated and included in the scope of this disclosure. At least some of these materials will adhere to the surfaces 110, 112 after setting and curing and without the use of a separate adhesive. In some examples, an adhesive is used, such as silicone rubber.

A shear stress sensor 114 (e.g., a MEMS shear stress sensor, such as a DIRECTSHEAR® sensor manufactured by IC²® of Gainesville, Fla.) is exposed to the surface 110, although in some examples, the shear stress sensor 114 is exposed to the surface 112. A support structure 124 supports a test specimen 120, such as a filter cake. The test specimen 120 also may comprise rock, metal, or other suitable materials. A filtrate port 122 couples the test specimen 120 to an exterior of the housing 102. A surface 128 of the test specimen 120 is exposed to the fluid in the fluid tank 118. As explained below, the rotational assembly may be moved back and forth (radially). As depicted in FIG. 1, the rotational assembly is shifted radially such that the outer surface of the shaft 104 abuts the surface 128 of the test specimen 120 at an interface 126. In at least some examples, a normal force is applied in a radial direction such that the rotational assembly is actively pressed against the test specimen 120 at the interface 126.

Figure 2:
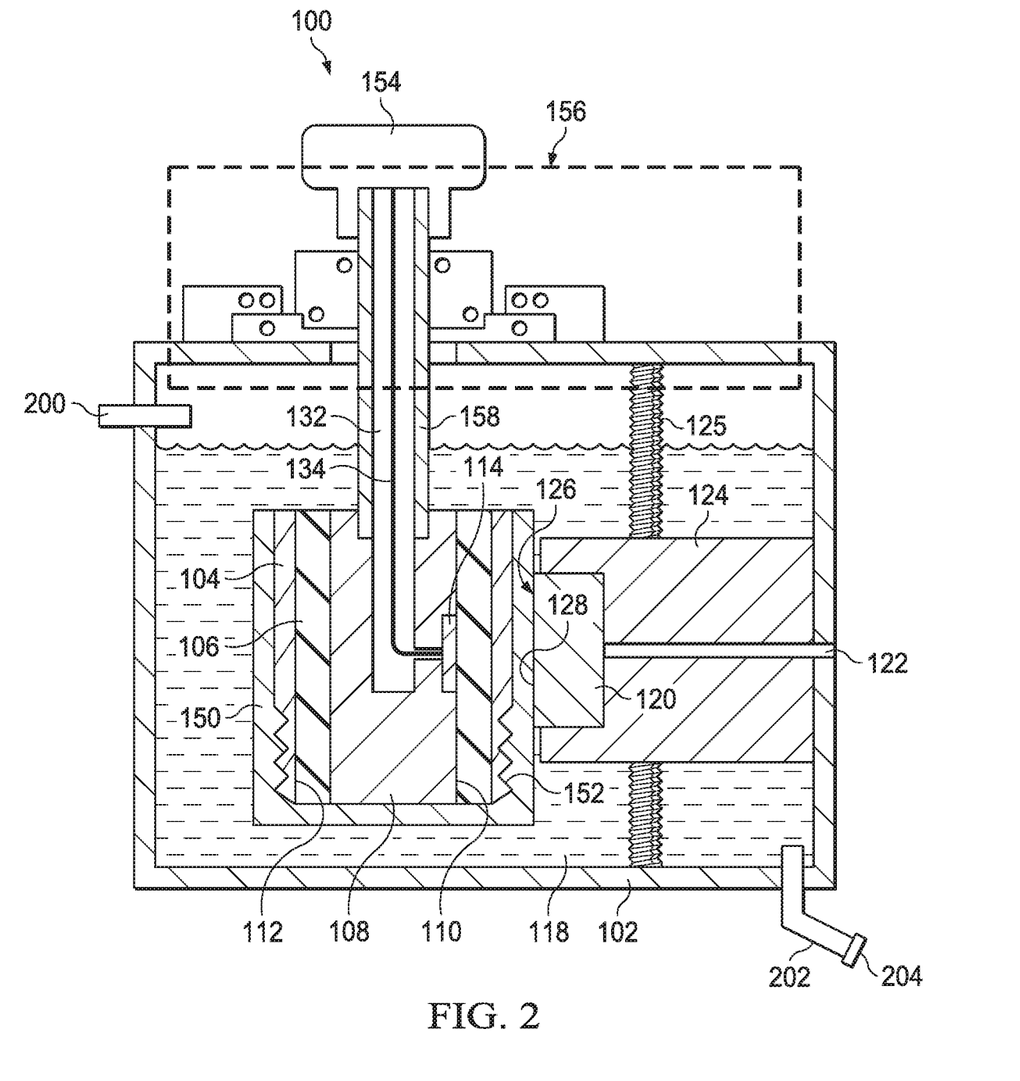
FIG. 2 is a profile cross-sectional view of a lubricity testing device, in accordance with various examples.

FIG. 2 is a profile cross-sectional view of the LTD 100, in accordance with various examples. In addition to the features depicted in FIG. 1, the view of FIG. 2 additionally depicts a control assembly 156 that controls the rotational assembly. The control assembly 156 includes a motor 154 and a shaft 158 that couples to and is partially included in the rotational assembly. The control assembly 156 may be moved radially such that the rotational assembly also is moved radially. A normal force may be applied to the control assembly 156 or generated by the control assembly 156 such that the rotational assembly applies that normal force to the test specimen 120. The support structure 124 may be raised or lowered along one or more rails 125. The shear stress sensor 114 couples to a cable 134 that is routed to the housing of the motor 154 via a channel 132. The fluid tank 118 includes a fluid inlet 200 and a fluid outlet 202 having a valve 204 to prevent unintentional voiding of the fluid tank 118.

The example of FIG. 2 differs from that of FIG. 1 due to the presence of a sleeve 150. The sleeve 150 may comprise any suitable material, such as a metal or plastic. The sleeve 150 and the shaft 104 include threads 152 that facilitate coupling of the sleeve 150 to the shaft 104. The sleeve 150 is optional. Thus, when the sleeve 150 is used, the sleeve 150 is pressed against the test specimen 120 with the aforementioned normal force. Conversely, when the sleeve 150 is not used, the outer surface of the shaft 104 is pressed against the test specimen 120 with the aforementioned normal force. The sleeve 150 may be screwed onto and off of the shaft 104 by partially or fully disassembling the control assembly 156 and removing the rotational assembly from the fluid tank 118.

In operation, the aforementioned normal force is used to press the rotational assembly (e.g., the sleeve 150 or the shaft 104) against the test specimen 120. The motor 154 then rotates the rotational assembly. As the rotational assembly rotates, non-solid elements of the fluid in the fluid tank 118 flow through the test specimen 120 as filtrate and through the filtrate port 122 to an exterior of the housing 102 (e.g., into a separate container). Any suitable technique may be employed to provide a sufficient pressure differential between the tank 118 and the exterior of the housing 102 at the end of the filtrate port 122. Metals, rock, and other solid elements in the fluid accumulate on the surface 128 of the test specimen 120, for example, at and near the interface 126. The lubricity of the fluid in the fluid tank 118 affects the coefficient of friction between the test specimen 120 (including the solid accumulations on the surface 128) and the rotational assembly. Thus, the coefficient of friction is an indication of the lubricity of the fluid. The coefficient of friction may be determined using shear stress measurements. Specifically, friction between the rotational assembly and the test specimen 120 (including accumulations on the surface 128) imparts shear stress on the flexible coupling 106, as stress lines 116 indicate in FIG. 1. The shear stress sensor 114 measures this shear stress, generates an electrical signal indicating the shear stress measurement, and outputs the electrical signal on cable 134. The cable 134 may exit the motor housing and may couple to electronics (not expressly shown; e.g., a computer, wireless communication equipment, storage). Such electronics may, e.g., process measurements received from the shear stress sensor 114, log measurements received from the shear stress sensor 114, etc. For example, the electronics may use the shear stress measurements to calculate the coefficient of friction:

$$\mu = \frac{\tau \pi r_1^3}{r_2 F_{normal}}$$

where $\mu$ is the coefficient of friction, $\tau$ is the shear stress measurement, $r_1$ is the distance from the center of the shaft 108 to the shear stress sensor 114 (i.e., the surface of the shear stress sensor 114 exposed to outer surface 110), $r_2$ is the distance from the center of the shaft 108 to the surface 128, and $F_{normal}$ is the normal force with which the shaft 104 (or sleeve 150) is pressed against the test specimen 120.

As explained, the coefficient of friction is an indicator of the lubricity of the fluid in the fluid tank 118. These and other calculable values may be logged in the electronics (e.g., computer), displayed on a display, etc.

Figure 3A:
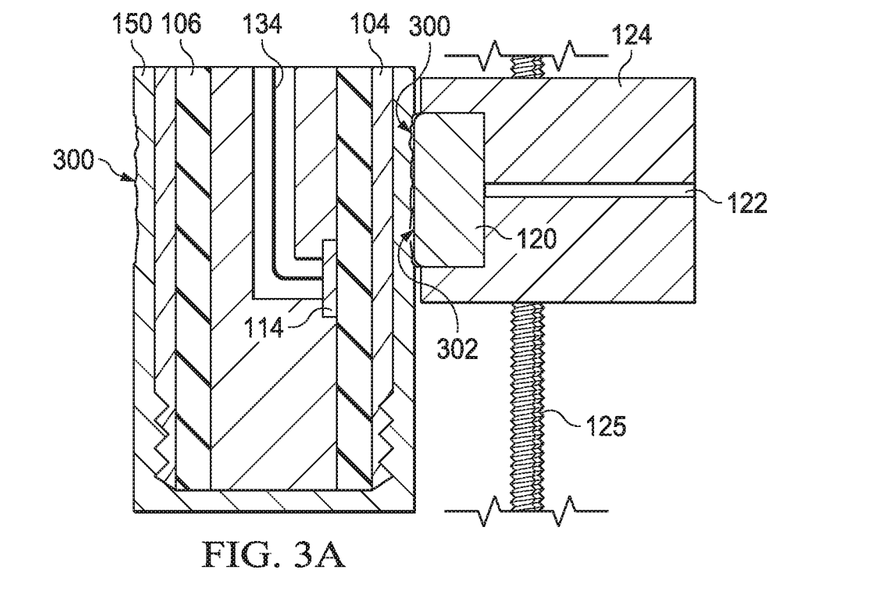
FIGS. 3A and 3B are profile cross-sectional views of a lubricity testing device depicting adjustment of components in the device, in accordance with various examples.
Figure 3B:
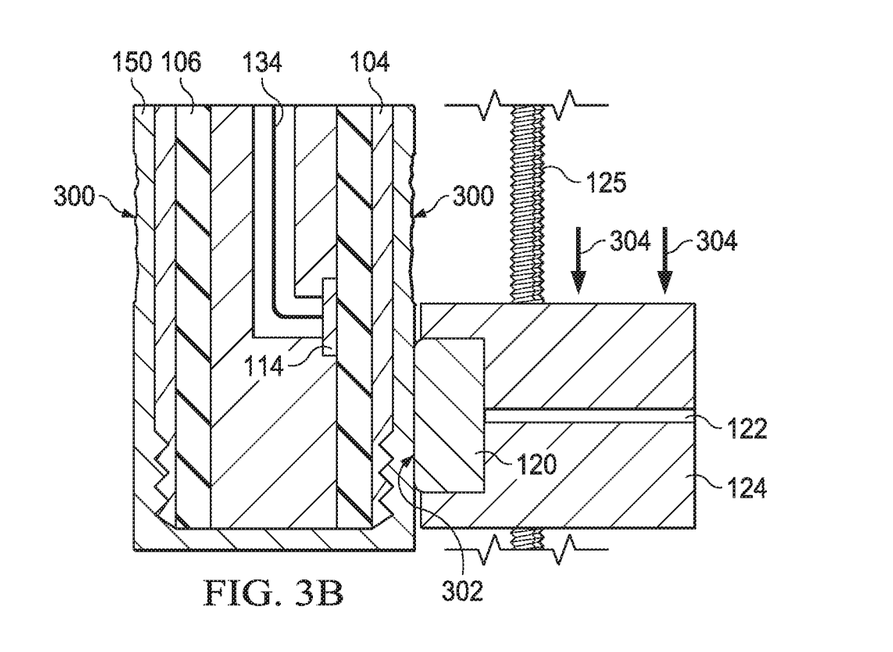

FIGS. 3A and 3B are profile cross-sectional views of portions of a lubricity testing device. These drawings depict the adjustment of components in the device, in accordance with various examples. These drawings depict only a portion of the rotational assembly, the test specimen 120, and the support structure 124 to clarify that these components move relative to each other, regardless of which component moves. For example, as FIG. 3A depicts, over time the testing process may cause wear and tear on the sleeve 150, as numeral 300 depicts. This wear and tear may result, for instance, from friction with the test specimen 120, including the metal, rock, and other solid accumulations on the test specimen 120. To promote efficiency, speed, and ease of use, the relative positions of the test specimen 120 and the rotational assembly are shifted, such that the test specimen 120 is now aligned with an area 302 of the sleeve 150 that has not been worn down. This movement may be accomplished, for example, by lowering the support structure 124 along the one or more rails 125, as numerals 304 depict. In examples where the support structure 124 is raised and/or lowered, the filtrate port 122 may comprise a flexible tube or hose and the support structure 124 may contain a hollow area to permit movement of the filtrate port 122 as the support structure 124 is raised or lowered. Although FIGS. 3A and 3B depict wear on the sleeve 150, wear may also occur on the shaft 104, and a similar technique may be used to re-align the shaft 104 and the test specimen 120.

Figure 4A:
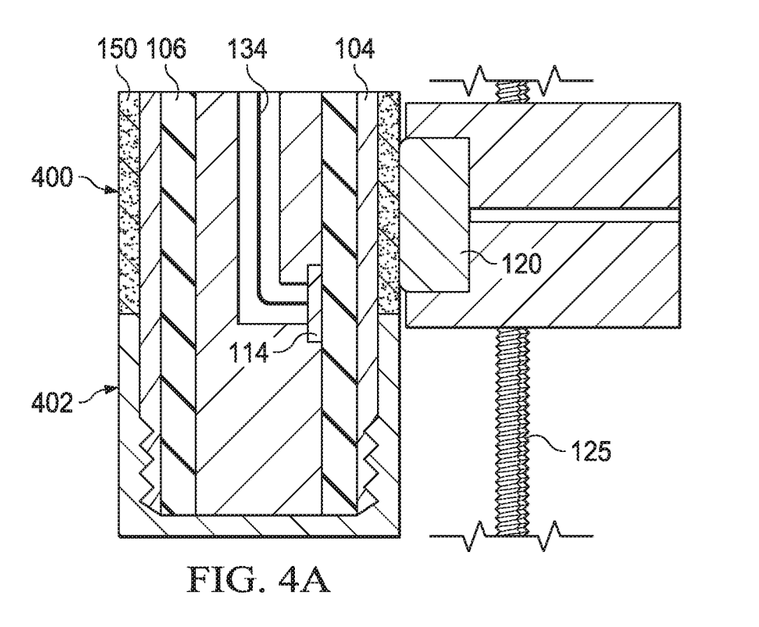
FIGS. 4A and 4B are profile cross-sectional views of a lubricity testing device depicting adjustment of components in the device, in accordance with various examples.
Figure 4B:
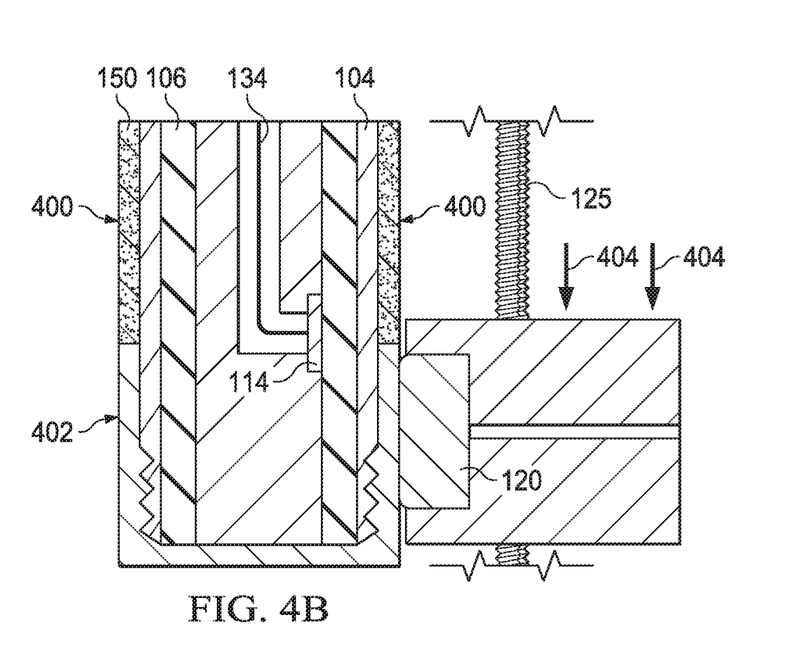

FIGS. 4A and 4B are profile cross-sectional views of a lubricity testing device. These drawings depict adjustment of components in the device, in accordance with various examples. These drawings depict only a portion of the rotational assembly, the test specimen 120, and the support structure 124 to clarify that these components move relative to each other, regardless of which component moves. The re-alignment depicted in FIGS. 4A and 4B is similar to that described above with respect to FIGS. 3A and 3B. The motivation for the re-alignment, however, differs from that of FIGS. 3A and 3B. In FIGS. 3A and 3B, the re-alignment is performed because of excessive wear on a portion of the sleeve 150 (or shaft 104), as numeral 300 depicts. In contrast, in FIGS. 4A and 4B, the re-alignment is performed because the sleeve 150 (or, in some examples, the shaft 104) has multiple, non-overlapping segments 400, 402, with each segment composed of different materials. For example, the lubricity testing may be performed with a first material in segment 400, and the lubricity testing may subsequently be performed for any of a variety of reasons with a second material in segment 402. Numerals 404 indicate the adjustment.

Figure 5:
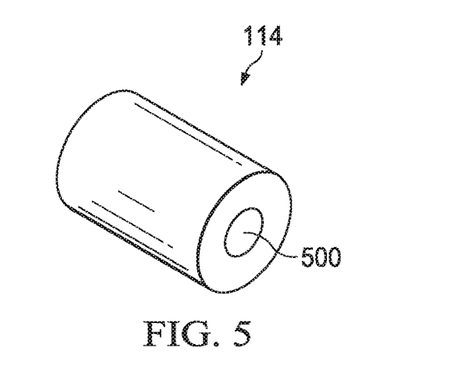
FIG. 5 is a perspective view of a shear stress sensor, in accordance with various examples.
Figure 6:
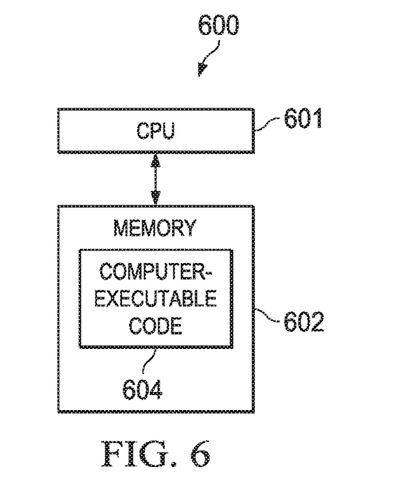
FIG. 6 is a schematic diagram of processing logic usable with the lubricity testing devices described herein, in accordance with various examples.

FIG. 5 is a perspective view of a shear stress sensor 114 (e.g., a MEMS shear stress sensor, such as the DIRECTSHEAR® sensor by IC²® in Gainesville, Fla.), in accordance with various examples. The shear stress sensor 114 includes a sensing surface 500 which, when abutting a flexible coupling (e.g., flexible coupling 106), measures the shear stress present in the flexible coupling and outputs an electrical signal indicating the measured shear stress. In some examples, the thickness of the shear stress sensor 114 as measured from the sensing surface 500 to the opposing, parallel surface of the shear stress sensor 114 is, e.g., less than or equal to 25 millimeters FIG. 6 is a schematic diagram of processing logic 600 usable with the lubricity testing devices described herein, in accordance with various examples. The processing logic 600 includes a central processing unit (CPU) 601 that couples to memory 602 (e.g., random access memory, read-only memory), as shown in FIG. 6. In at least some such examples, the memory 602 stores computer-executable code 604, which, when executed by the CPU 601, causes the CPU 601 to perform some or all of the functions described herein, including the functions described below with reference to FIG. 7. In some examples, the processing logic 600 comprises a field programmable gate array ("FPGA"), which may be programmed using an appropriate bitstream to cause it to perform some or all of the functions described herein. In some examples, the processing logic 600 comprises a combination of an FPGA and the components depicted in FIG. 6, with the combination operating in tandem to perform some or all of the functions described herein. Any and all such combinations are contemplated and included in the scope of this disclosure. In at least some examples, the processing logic 600 couples to the cable 134 described and depicted herein such that it receives shear stress measurements from shear stress sensors.

Figure 7:
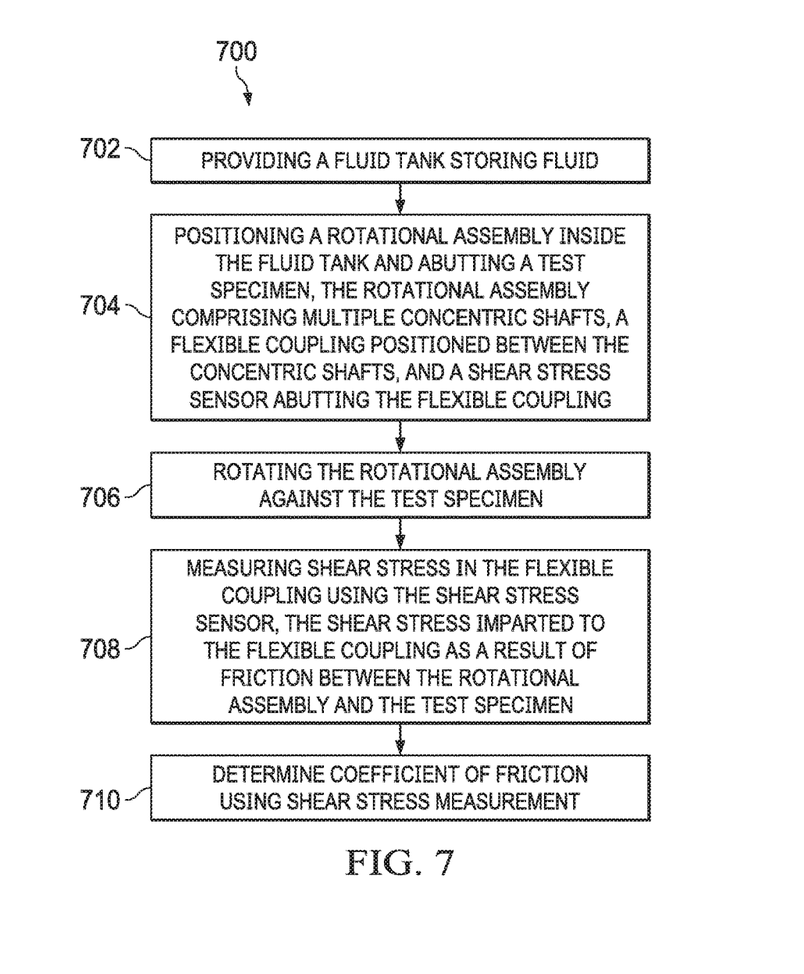
FIG. 7 is a flow diagram of a method for operating a lubricity testing device, in accordance with various examples.

FIG. 7 is a flow diagram of a method 700 for operating a lubricity testing device, in accordance with various examples. The method 700 begins by providing a fluid tank storing fluid to be tested (step 702). The method 700 next comprises positioning a rotational assembly inside the fluid tank and abutting a test specimen (step 704). The rotational assembly comprises multiple concentric shafts, a flexible coupling positioned between the concentric shafts, and a shear stress sensor abutting the flexible coupling. The method 700 also comprises rotating the rotational assembly against the test specimen (step 706) and measuring shear stress in the flexible coupling using the shear stress sensor (step 708). The shear stress is imparted to the flexible coupling as a result of friction between the rotational assembly and the test specimen. The method 700 then comprises determining the coefficient of friction using the shear stress measurement (step 710).

In the foregoing discussion and in the claims, the terms "including" and "comprising" are used in an open-ended fashion, and thus should be interpreted to mean "including, but not limited to . . . ." Unless otherwise stated, "about," "approximately," or "substantially" preceding a value means+/−10 percent of the stated value. The above discussion is meant to be illustrative of the principles and various examples of the present disclosure. Numerous variations and modifications will become apparent to those skilled in the art once the above disclosure is fully appreciated. It is intended that the following claims be interpreted to embrace all such variations and modifications.

In some examples, a lubricity testing device comprises a fluid tank and a rotational assembly positioned within the fluid tank. The rotational assembly, in turn, comprises a first shaft, a second shaft positioned within the first shaft, and a flexible coupling positioned between the first and second shafts. The flexible coupling is coupled to a first surface of the first shaft and to a second surface of the second shaft. The rotational assembly further comprises a shear stress sensor abutting the flexible coupling. The lubricity testing device also includes a test specimen abutting the rotational assembly. The lubricity testing device may be supplemented using one or more of the following concepts, in any order and in any combination: wherein the shear stress sensor comprises a micro-electro-mechanical system (MEMS) shear stress sensor; wherein the shear stress sensor is exposed to the second surface of the second shaft; wherein the shear stress sensor is exposed to the first surface of the first shaft; wherein the device comprises a filtrate port coupled to the test specimen and exposed to an exterior of the device; wherein the flexible coupling is selected from the group consisting of: silicone rubber; urethane rubber; natural rubber; styrene-butadiene rubber; butylrubber; and combinations thereof; wherein the rotational assembly further comprises a sleeve coupled to an exterior of the first shaft; wherein the sleeve abuts the test specimen; wherein the sleeve comprises threading mated to threading on the first shaft; wherein a first segment of the sleeve is composed of a first material and a second segment of the sleeve is composed of a second material, and wherein the first and second segments do not overlap; wherein the first shaft abuts the test specimen; further comprising a fluid inlet to the fluid tank and a fluid outlet from the fluid tank, the fluid outlet including a valve; wherein the test specimen comprises a filter cake.

In some examples, a method comprises providing a fluid tank storing fluid and positioning a rotational assembly inside the fluid tank and abutting a test specimen, the rotational assembly comprising multiple concentric shafts, a flexible coupling positioned between the concentric shafts, and a shear stress sensor abutting the flexible coupling. The method also comprises rotating the rotational assembly against the test specimen and measuring shear stress in the flexible coupling using the shear stress sensor. The shear stress is imparted to the flexible coupling as a result of friction between the rotational assembly and the test specimen. The method may be supplemented using one or more of the following concepts, in any order and in any combination: wherein rotating the rotational assembly against the test specimen comprises rotating a first segment of a sleeve of the rotational assembly against the test specimen, and further comprising: adjusting an alignment between the rotational assembly and the test specimen; and after the adjustment, rotating a second segment of the sleeve against the test specimen; wherein the first segment and the second segment are composed of different materials and are non-overlapping; wherein the shear stress sensor comprises a micro-electro-mechanical system (MEMS) shear stress sensor; wherein the flexible coupling is selected from the group consisting of: silicone rubber; urethane rubber; natural rubber; styrene-butadiene-rubber; butylrubber; polyurethane; polychloroprene; nitrile; hydrogenated nitrile; chlorosulphonated polyethylene; fluorosilicone; fluorocarbon; and combinations thereof; wherein the shear stress sensor is exposed to a surface of a shaft of the multiple concentric shafts, and wherein the surface of the shaft faces away from a longitudinal axis of the multiple concentric shafts; further comprising calculating a coefficient of the friction between the rotational assembly and the test specimen based on a normal force with which the rotational assembly is pressed against the test specimen and on the shear stress measurement.

What is claimed is:
1. A lubricity testing device, comprising:
   a fluid tank;
   a rotational assembly positioned within the fluid tank and comprising:
      a first shaft;
      a second shaft positioned within the first shaft;
      a flexible coupling positioned between the first and second shafts, the flexible coupling coupled to a first surface of the first shaft and to a second surface of the second shaft; and
      a shear stress sensor abutting the flexible coupling; and
   a test specimen abutting the rotational assembly.
2. The device of claim 1, wherein the shear stress sensor comprises a micro-electro-mechanical system (MEMS) shear stress sensor.
3. The device of claim 1, wherein the shear stress sensor is exposed through the second surface of the second shaft.

4. The device of claim 1, wherein the shear stress sensor is exposed to the first surface of the first shaft at an interface of a shear stress line.

5. The device of claim 1, wherein the device comprises a filtrate port coupled to the test specimen and exposed to an exterior of the device.

6. The device of claim 1, wherein the flexible coupling is selected from the group consisting of: silicone rubber; urethane rubber; natural rubber; styrene-butadiene rubber; butylrubber; and combinations thereof.

7. The device of claim 1, wherein the rotational assembly further comprises a sleeve coupled to an exterior of the first shaft.

8. The device of claim 7, wherein the sleeve abuts the test specimen.

9. The device of claim 7, wherein the sleeve comprises threading mated to threading on the first shaft.

10. The device of claim 7, wherein a first segment of the sleeve is composed of a first material and a second segment of the sleeve is composed of a second material, and wherein the first and second segments do not overlap.

11. The device of claim 1, wherein the first shaft abuts the test specimen.

12. The device of claim 1, further comprising a fluid inlet to the fluid tank and a fluid outlet from the fluid tank, the fluid outlet including a valve.

13. The device of claim 1, wherein the test specimen comprises a filter cake.

14. A method, comprising:
providing a fluid tank storing fluid;
positioning a rotational assembly inside the fluid tank and abutting a test specimen, the rotational assembly comprising multiple concentric shafts, a flexible coupling positioned between the concentric shafts, and a shear stress sensor abutting the flexible coupling;
rotating the rotational assembly against the test specimen; and
measuring shear stress in the flexible coupling using the shear stress sensor, the shear stress imparted to the flexible coupling as a result of friction between the rotational assembly and the test specimen.

15. The method of claim 14, wherein rotating the rotational assembly against the test specimen comprises rotating a first segment of a sleeve of the rotational assembly against the test specimen, and further comprising:
adjusting an alignment between the rotational assembly and the test specimen; and
after the adjustment, rotating a second segment of the sleeve against the test specimen.

16. The method of claim 15, wherein the first segment and the second segment are composed of different materials and are non-overlapping.

17. The method of claim 14, wherein the shear stress sensor comprises a micro-electro-mechanical system (MEMS) shear stress sensor.

18. The method of claim 14, wherein the flexible coupling is selected from the group consisting of: silicone rubber; urethane rubber; natural rubber; styrene-butadiene-rubber; butylrubber; polyurethane; polychloroprene; nitrile; hydrogenated nitrile; chlorosulphonated polyethylene; fluorosilicone; fluorocarbon; and combinations thereof.

19. The method of claim 14, wherein the shear stress sensor is exposed through the second surface of the second shaft.

20. The method of claim 14, further comprising calculating a coefficient of the friction between the rotational assembly and the test specimen based on a normal force with which the rotational assembly is pressed against the test specimen and on the shear stress measurement.

* * * * *